US009335271B2

(12) United States Patent
Pruessner et al.

(10) Patent No.: US 9,335,271 B2
(45) Date of Patent: May 10, 2016

(54) CAVITY OPTO-MECHANICAL SENSOR SYSTEM

(71) Applicants: Marcel W. Pruessner, Silver Spring, MD (US); Todd H. Stievater, Arlington, VA (US); William S. Rabinovich, Silver Spring, MD (US)

(72) Inventors: Marcel W. Pruessner, Silver Spring, MD (US); Todd H. Stievater, Arlington, VA (US); William S. Rabinovich, Silver Spring, MD (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/466,090

(22) Filed: Aug. 22, 2014

(65) Prior Publication Data

US 2015/0323466 A1    Nov. 12, 2015

Related U.S. Application Data

(62) Division of application No. 13/945,075, filed on Jul. 18, 2013, now Pat. No. 8,848,197, which is a division of application No. 12/729,482, filed on Mar. 23, 2010, now Pat. No. 8,542,365.

(60) Provisional application No. 61/162,373, filed on Mar. 23, 2009.

(51) Int. Cl.
| | |
|---|---|
| *G01B 9/02* | (2006.01) |
| *G01N 21/75* | (2006.01) |
| *G01G 3/16* | (2006.01) |
| *G01N 29/036* | (2006.01) |
| *G01N 21/17* | (2006.01) |

(52) U.S. Cl.
CPC ............ *G01N 21/75* (2013.01); *G01B 9/02004* (2013.01); *G01B 9/02051* (2013.01); *G01G 3/165* (2013.01); *G01N 21/17* (2013.01); *G01N 29/036* (2013.01); *G01B 2290/25* (2013.01); *G01N 2021/757* (2013.01); *G01N 2291/0256* (2013.01)

(58) Field of Classification Search
CPC ................ G01N 21/17; G01N 29/036; G01N 2291/0256; G01B 9/02004; G01B 9/02051; G01B 2290/25; G01G 3/165
USPC .................................. 356/454, 479, 480, 506
See application file for complete search history.

(56) References Cited

U.S. PATENT DOCUMENTS

| | | | | |
|---|---|---|---|---|
| 4,856,859 | A * | 8/1989 | Imoto ........................... 385/129 |
| 5,859,866 | A * | 1/1999 | Forrest et al. ............ 372/50.124 |
| 2005/0046860 | A1* | 3/2005 | Waagaard et al. ............ 356/478 |
| 2008/0049228 | A1* | 2/2008 | Chan ............................. 356/454 |
| 2010/0085572 | A1* | 4/2010 | Hartog .......................... 356/478 |

* cited by examiner

*Primary Examiner* — Tarifur Chowdhury
*Assistant Examiner* — Jonathon Cook
(74) *Attorney, Agent, or Firm* — US Naval Research Laboratory; Richard F. Bis

(57) ABSTRACT

A mass sensor system including multiple Fabry-Perot microcavities connected in parallel by multiple waveguides. Each of the mass sensors includes a microbridge having a fundamental resonance frequency, and a movable reflective mirror etched into the microbridge; a fixed reflective mirror etched in a substrate, the fixed reflective mirror being fixed to the substrate in a region spaced apart from the movable reflective mirror; and an optical waveguide etched in the substrate that connects the movable mirror and the fixed mirror forming the Fabry-Perot microcavity interferometer. The system includes a tunable continuous-wave laser operative to optically interrogate the Fabry-Perot microcavity of each of the plurality of mass sensors, and a receiver operative to receive sensor signals from each of the plurality of mass sensors, the sensor signals comprising reflective signals and transmitted signals. A continuous-wave laser may generate optical forces that modify the motion, dynamics, or mechanical Q-factor of the microbridge.

20 Claims, 12 Drawing Sheets

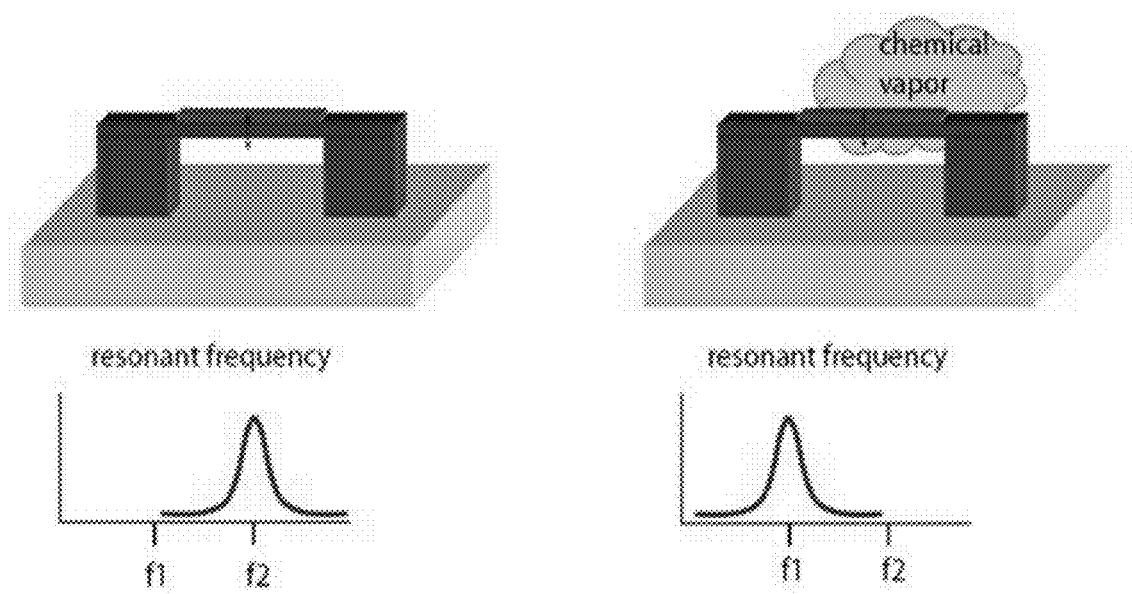
Figure 1A – Prior Art             Figure 1B – Prior Art

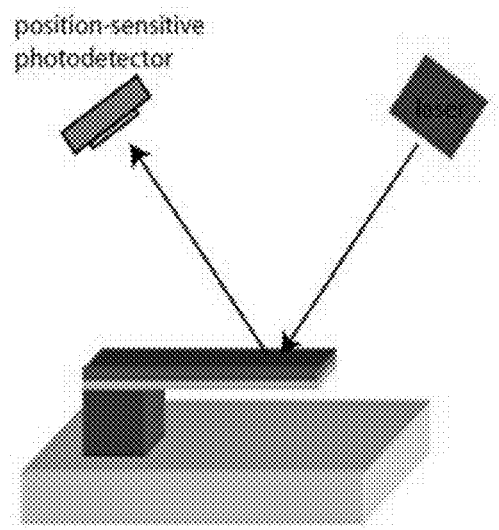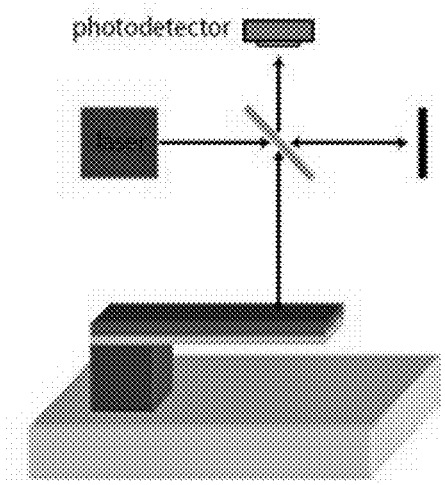
Figure 2A – Prior Art			Figure 2B – Prior Art

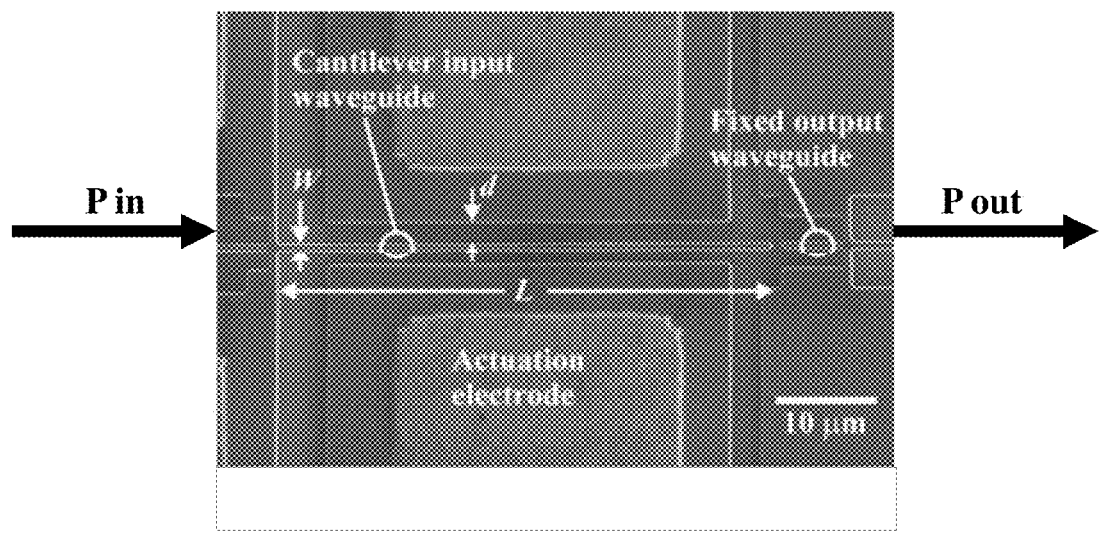
Figure 3A – Prior Art
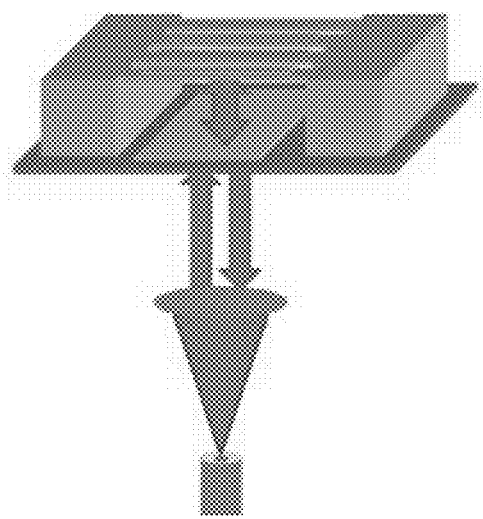
Figure 3B – Prior Art

CAVITY OPTO-MECHANICAL SENSOR SYSTEM

CROSS-REFERENCE TO RELATED APPLICATIONS

This application is a divisional application of U.S. Non-Provisional patent application entitled, "CAVITY OPTO-MECHANICAL SENSOR ARRAY," which was filed on Jul. 18, 2013, and assigned U.S. application Ser. No. 13/945,075, which is a divisional application of U.S. Non-Provisional patent application entitled, "OPTICAL MEMS CHEMICAL SENSOR ARRAY," which was filed on Mar. 23, 2010, and assigned U.S. application Ser. No. 12/710,482; and, which claims priority to provisional patent application entitled, "Micro-Electro-Mechanical Chemical Sensor Array With Waveguide Interconnects and On-Chip Interferometric Optical Readout," filed on Mar. 23, 2009, and assigned U.S. Application No. 61/162,373; the entire contents of which are hereby incorporated by reference.

FIELD OF THE INVENTION

The invention relates generally to micro-electro-mechanical systems (MEMS) based sensors. More specifically, the invention relates to a MEMS based sensor with waveguide interconnects and integrated interferometric optical readout.

BACKGROUND

Micro-electromechanical systems (MEMS) are micro-mechanical transducers. MEMS actuators can take an electrical signal and convert it into a mechanical signal (e.g. movement). Conversely, MEMS sensors can take a mechanical signal (e.g. displacement or frequency) and can transfer that signal to an electrical or optical carrier. MEMS chemical sensors generally consist of a cantilever beam or bridge that is coated with a chemo-selective polymer, whose displacement and/or resonant frequency can be continuously monitored. Changes in the environment's chemical composition can affect the mechanical behavior of the MEMS sensor. Therefore, the MEMS sensor can provide a convenient means for transducing signals arising from the presence of chemical agents in the environment into measurable electrical or optical signals. FIG. 1A is a schematic of a prior art microbridge resonator and mechanical resonance spectrum.

For example, in one approach (i.e., static mode), upon chemical exposure, the chemo-selective polymer can selectively adsorb an analyte and the induced strain can result in beam bending, or displacement. A second approach (i.e., dynamic mode) can rely on exciting the mechanical resonances of the MEMS sensor. Upon chemical exposure, the polymer can selectively adsorbs the analyte and the resulting mass loading and induced strain shifts the resonance frequencies. FIGS. 1A and 1B are schematics of a prior art microbridge resonator and mechanical resonance spectrum, reflecting the downshift of mechanical resonance upon chemical vapor exposure, in accordance with the dynamic mode approach discussed.

Some advantages of a MEMS sensor can include: (1) high displacement sensitivity—simple (noninterferometric) optical readout enables displacement measurements of the order of 1 nm, (2) small mass, which makes the devices highly sensitive to any adsorbed chemical and hence mass loading—attogram mass changes have been measured, (3) small size—13×13 cantilever arrays with each element with area A<100 μm×100 μm have been realized, and (4) high selectivity—sensor arrays with multiple chemo-selective coatings enable detection of multiple analytes.

Various readout methods for interrogating the mechanical behavior of a MEMS sensor have been demonstrated. For example, one method takes advantage of piezo-resistance; the resistance across a micromechanical resonator changes with displacement and induced strain. The resistance change is small and generally requires two cantilever piezoresistors in a Wheatstone bridge configuration along with a differential amplifier to measure resonance. Similarly, in another method, a capacitive readout requires integrated amplifiers to convert a capacitance modulation into a measurable resonance frequency. Finally, the displacement amplitude for capacitive readout is generally in the tens of nanometers, which may require significant power to excite and measure the mechanical resonances.

Optical MEMS Sensors with Off-Chip Detection

Compared to electrical methods, optical methods can be completely passive and allow for remote readout via free-space or optical fibers. For example, a common optical detection method can utilize a position-sensitive photodetector in conjunction with a laser beam focused on the tip of the resonator. As the cantilever bends or oscillates, the reflected laser beam is deflected, modulated, and read out by the photodetector. FIG. 2A is a schematic of an optical displacement readout using a position sensitive photodetector. While this method is reasonably sensitive (displacements of one nanometer can be measured) and potentially enables remote readout, it typically requires accurate alignment between the probe laser and micro-resonator and cannot be packaged compactly due to the requirement of a long optical lever arm.

Another optical readout method can utilize interferometry to measure small displacements. For example, a Michelson interferometric readout setup can take advantage of interference between a reference laser beam and a second beam that is reflected off a cantilever that has been coated with a reflective metal. FIG. 2B is a schematic of an optical readout using an off-chip Michelson interferometer. Interference between the two beams can enable measurement of displacements many times smaller than the wavelength of light, λ, used in the experiment. In fact, displacements of the order of 10 picometers can be measured using interferometric techniques. However, a potential limitation with this approach is the need for precision alignment of the interferometer with the cantilever. Furthermore, it is not possible to interrogate multiple sensors (cantilevers) using a single off-chip interferometer. Multiple sensors require multiple interferometers, making it virtually impossible to develop large sensor arrays utilizing this particular optical readout method.

Optical MEMS Sensors with on-Chip Detection

In order to develop large sensor arrays, an on-chip optical readout is needed. By incorporating an optical waveguide onto the resonator, i.e. a cantilever waveguide, along with a second fixed waveguide, the device can be self-aligned during fabrication (provided there is no cantilever deflection due to intrinsic strain). This eliminates the need for accurate alignment required by the optical readout methods, as pictured in FIG. 2A and FIG. 2B. By sending laser light through the waveguides, any cantilever motion modulates the optical power coupled between the waveguides. FIG. 3A is a schematic representing a cantilever waveguide on-chip optical readout, in accordance with the prior art. Sub-nanometer displacement, mass loading, chemical sensing, and microfluidic flow rate measurements have been demonstrated with this approach. However, a potential drawback that still exists is the nonlinear response with waveguide displacement, which limits the sensitivity.

The highest displacement measurement resolution is obtained using interferometry, an approach that finds application in a variety of areas ranging from accelerometers to detection of gravity waves to mesoscopic quantum physics measurements. An external, off-chip, interferometric readout setup was described previously in relation to FIG. 2B. By making the micromechanical resonator reflective and coupling it to a second fixed mirror, an on-chip Fabry-Perot microcavity interferometer can be formed. FIG. 3B is a schematic representing an on-chip vertical-cavity Fabry-Perot interferometric readout, in accordance with the prior art. If the mirror reflectance is large, then the microcavity can have high finesse, and small displacements of the mirror can result in large changes in optical response. For example, displacements (e.g., <<1 nm) much smaller than the laser wavelength (e.g., $\lambda \approx 1550$ nm) can be measured. Also, the device is alignment free by design, allowing a simple setup. However, a drawback with this approach is the limited number of sensors that can be incorporated in a single-chip array. For example, previous MEMS chemical sensors with on-chip interferometric readout utilized a 1×4 array of optical microcavities vertical to the substrate. On the other hand, arrays with many (e.g., hundreds or more) of sensors may be difficult to achieve due to challenges in the interrogation of multiple vertical cavities with a single laser beam.

BACKGROUND SUMMARY

In summary, technological trends in MEMS sensors have led to devices that contain on-chip optical readouts that can measure very small displacements. However, the current approaches limit the number of sensors that can be incorporated in a single chip array.

Accordingly, there remains a need for a device that has an integrated optical readout, that builds upon the prior art inventions discussed above. This device would enable multiple sensors (e.g., hundreds or more) to be interconnected on a single chip with a single input/output signal from an optical fiber. Additionally, the device would be compact, lightweight, highly selective sensor arrays with potentially hundreds of sensors on a single chip.

SUMMARY OF THE INVENTION

The disclosed MEMS sensor includes an optical readout function that relies on an on-chip integrated waveguide Fabry-Perot microcavity interferometer. Integrated waveguides enable multiple sensors to be interconnected on a single chip with a single input/output signal from an optical fiber. Consequently, this invention enables compact, lightweight, highly selective sensor arrays with potentially hundreds of sensors on a single chip. Any individual sensor in the array can potentially be read out using a single optical fiber. Another advantage is the high-finesse waveguide Fabry-Perot optical microcavity, which enables the detection of displacements in the picometer range. This high sensitivity enables passive operation with no electrical power required. The Fabry-Perot interferometer also enables the wavelength-selective interrogation of individual sensors in a sensor array. Finally, the device can be operated in transmission as well as in reflection mode, which allows for increased flexibility when inserting large numbers of sensors into a fiber optic network.

These and other aspects, objects, and features of the present invention will become apparent from the following detailed description of the exemplary embodiments, read in conjunction with, and reference to, the accompanying drawings.

BRIEF DESCRIPTION OF THE DRAWINGS

FIG. 1A is a schematic of a microbridge resonator and mechanical resonance spectrum, in accordance with the prior art.

FIG. 1B is a schematic of a microbridge resonator and mechanical resonance spectrum, reflecting the downshift of mechanical resonance upon chemical vapor exposure, in accordance with the prior art.

FIG. 2A is a schematic of an optical displacement readout using a position sensitive photodetector, in accordance with the prior art.

FIG. 2B is a schematic of an optical readout using an off-chip Michelson interferometer, in accordance with the prior art.

FIG. 3A is a schematic of a cantilever waveguide on-chip optical readout, in accordance with the prior art.

FIG. 3B is a schematic of an on-chip vertical-cavity Fabry-Perot interferometric readout, in accordance with the prior art.

DETAILED DESCRIPTION OF EXEMPLARY EMBODIMENTS

Figure 4:
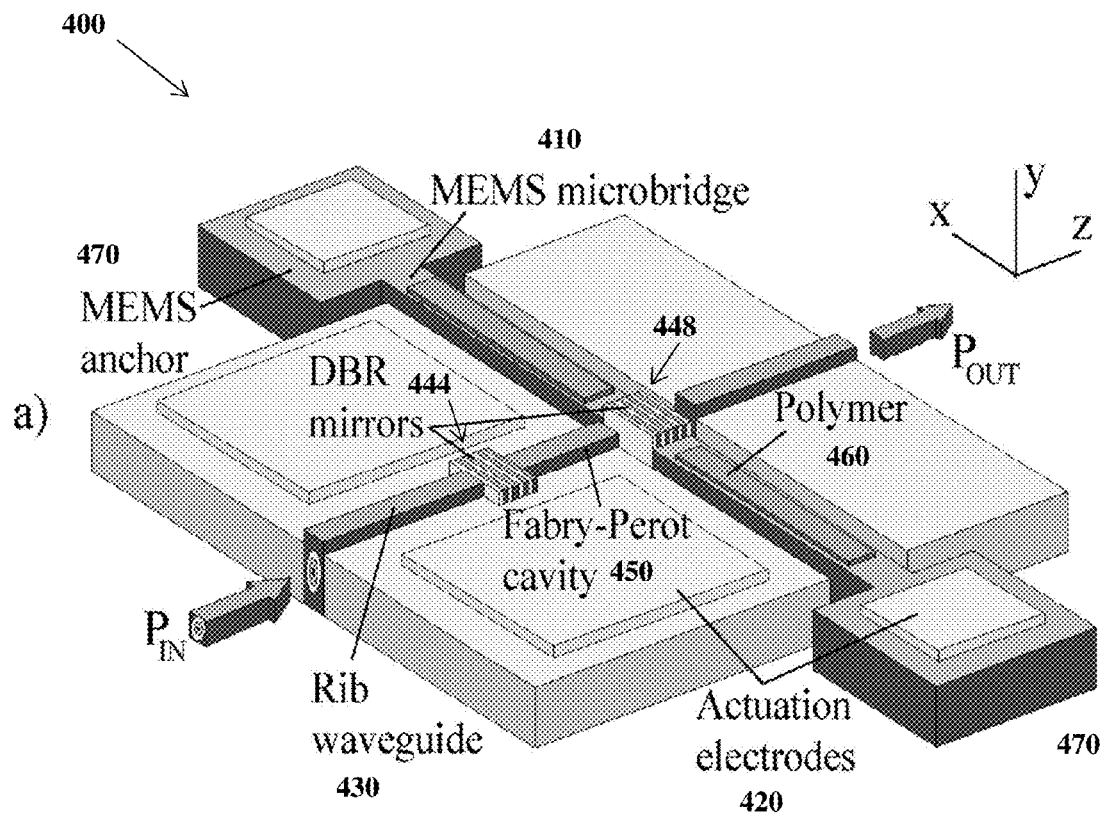
FIG. 4 is a schematic of an optical MEMS chemical sensor in accordance with an exemplary embodiment of the invention.

Referring now to the drawings, in which like numerals represent like elements, aspects of the exemplary embodiments will be described in connection with the drawing set.

The present invention has the advantage of enabling the interconnection of many (e.g., potentially hundreds or more) sensors via integrated optical waveguides. At the same time, extremely high displacement sensitivity can be obtained via interferometry using an integrated Fabry-Perot microcavity interferometer. To take advantage of both of these features, an in-plane waveguide Fabry-Perot microcavity interferometer is utilized. One of ordinary skill in the art will understand that a Fabry-Perot microcavity interferometer can be known by other interchangeable names with the same meaning, such as Fabry-Perot microcavity, Fabry-Perot cavity, Fabry-Perot etalon cavity, Fabry-Perot optical cavity, as well as others.

FIG. 4 is a schematic of a MEMS sensor 400 in accordance with an exemplary embodiment of the invention. The MEMS sensor 400 can include a MEMS microbridge 410, actuation electrodes 420 for applying an AC bias voltage to electrostatically drive the microbridge resonances, a rib waveguide 430 for coupling laser light to the device for remote optical interrogation, distributed Bragg reflector (DBR) mirrors 444, 448 that form a Fabry-Perot microcavity interferometer 450, and a polymer coating 460 deposited on the microbridge for chemo-selective adsorption of analytes.

More specifically, the MEMS microbridge 410 can be a microbridge, microbeam, or cantilever. A microbridge is a semiconductor microbeam that can be attached to support posts on both ends of the semiconductor microbeam. More specifically, the microbridge 410 can include a semiconductor microbeam fabricated from silicon-on-insulator that is suspended above an underlying $SiO_2$ insulator that can be selectively etched leaving one or more $SiO_2$ posts, or support posts 470, at the two ends of the semiconductor microbeam. The support posts 470 connect each end of the semiconductor microbeam to the substrate to maintain the microbridge and movable reflective mirror at a distance from the fixed reflective mirror. However, in an alternative embodiment, a microbeam that is only supported at one end (i.e., a cantilever) can also be used. In an exemplary embodiment of the MEMS sensor 400, the MEMS microbridge 410 can have the dimensions of width, W=3 µm, and length, L=400 µm. Additionally, the microbridge 410 can have a fundamental resonance frequency.

The polymer coating 460 deposited on the microbridge for chemoselective adsorption of analytes can be a layer of chemoselective material. The addition of the chemoselective polymer coating 460 enables the device 400 to function as a sensor. In an exemplary embodiment, the layer of chemoselective material deposited on the microbridge can be disposed on a surface of the microbridge that is opposite the surface of the microbridge that faces the substrate, and the chemoselective polymer can be polyethyleneimine.

The MEMS sensor 400 can include two DBR mirrors 444 and 448. One of the DBR mirrors 444 can be a fixed reflective mirror etched in a substrate. The fixed reflective mirror 444 can be fixed to the substrate in a region spaced apart from the microbridge 410. The other DBR mirror 448 can be a movable reflective mirror that is attached to the microbridge 410. More specifically, the movable reflective mirror 448 can be etched in a selected region of the microbridge 410 at a distance from the fixed reflective mirror 444. In an exemplary embodiment, the selected region of the microbridge 410 where the movable reflective mirror 448 is etched, or attached, can be at the center of the microbridge 410.

DBR mirrors are a unique type of mirror typically formed from periodically alternating layers with different refractive index. The layers can be formed by etching air trenches vertically in the silicon substrate. That is, the layers are a grating made of silicon and air trenches. While DBR mirrors are known to one of ordinary skill in the art, the use of etched Distributed Bragg reflector (DBR) gratings for mass sensors is novel.

The two DBR mirrors 444 and 448 can be connected by an optical waveguide 430 that is etched in the substrate. More specifically, the optical waveguide 430 can be a rib waveguide. The optical waveguide 430 can be etched in the substrate at an angle perpendicular, or substantially perpendicular, to the microbridge 410. Other angles between the optical waveguide 430 and microbridge 410 may also be used. The combination of the fixed reflective mirror 444, the movable reflective mirror 448, and the optical, or rib, waveguide 430 can form a Fabry-Perot microcavity interferometer, 450. One of ordinary skill in the art will understand that the term Fabry-Perot microcavity interferometer, can be used interchangeably with Fabry-Perot microcavity or Fabry-Perot etalon cavity.

The Fabry-Perot microcavity interferometer 450 as a whole is reflective, except at the resonant wavelengths of the Fabry-Perot microcavity interferometer 450. At the resonant wavelengths of the Fabry-Perot microcavity 450, the Fabry-Perot microcavity 450 can become highly transmissive with zero reflection. Thus, the Fabry-Perot microcavity 450 can be reflective or transmissive, depending on the wavelength. In an exemplary embodiment, the Fabry-Perot microcavity 449 can have a cavity length of $L_C$=3 µm, and a cavity width of $W_C$=6 µm.

In an exemplary embodiment, the sensor 400 can be fabricated in silicon-on-insulator with $t_{Silicon}$=4.8 µm and $t_{SiO2}$=1.0 µm. The process can utilize electron-beam and photolithography followed by ICP/RIE cryo-etching. Metal pads (e.g., Al/Ti/Au) can be defined by lift-off process. The chips can be thinned and cleaved to expose the waveguide facets followed by sacrificial BHF etching and critical point drying. Polyethylenimine (PEI) can be deposited on the microbridge using tungsten probe tips (e.g., radius, R≈1 µm), followed by an oven bake (e.g., 45° C., 24 hours). The ability to adsorb and concentrate an analyte is given by the partition coefficient, $K=C_S/C_V$, where $C_S$ is the analyte concentration in the sorbent phase (i.e. adsorbed by the polymer), and $C_V$ is the vapor phase concentration (i.e. in the environment). PEI's water vapor partition coefficient can be $K_{PEI,H2O}$≈100,000, which indicates high sensitivity.

Figure 5A:
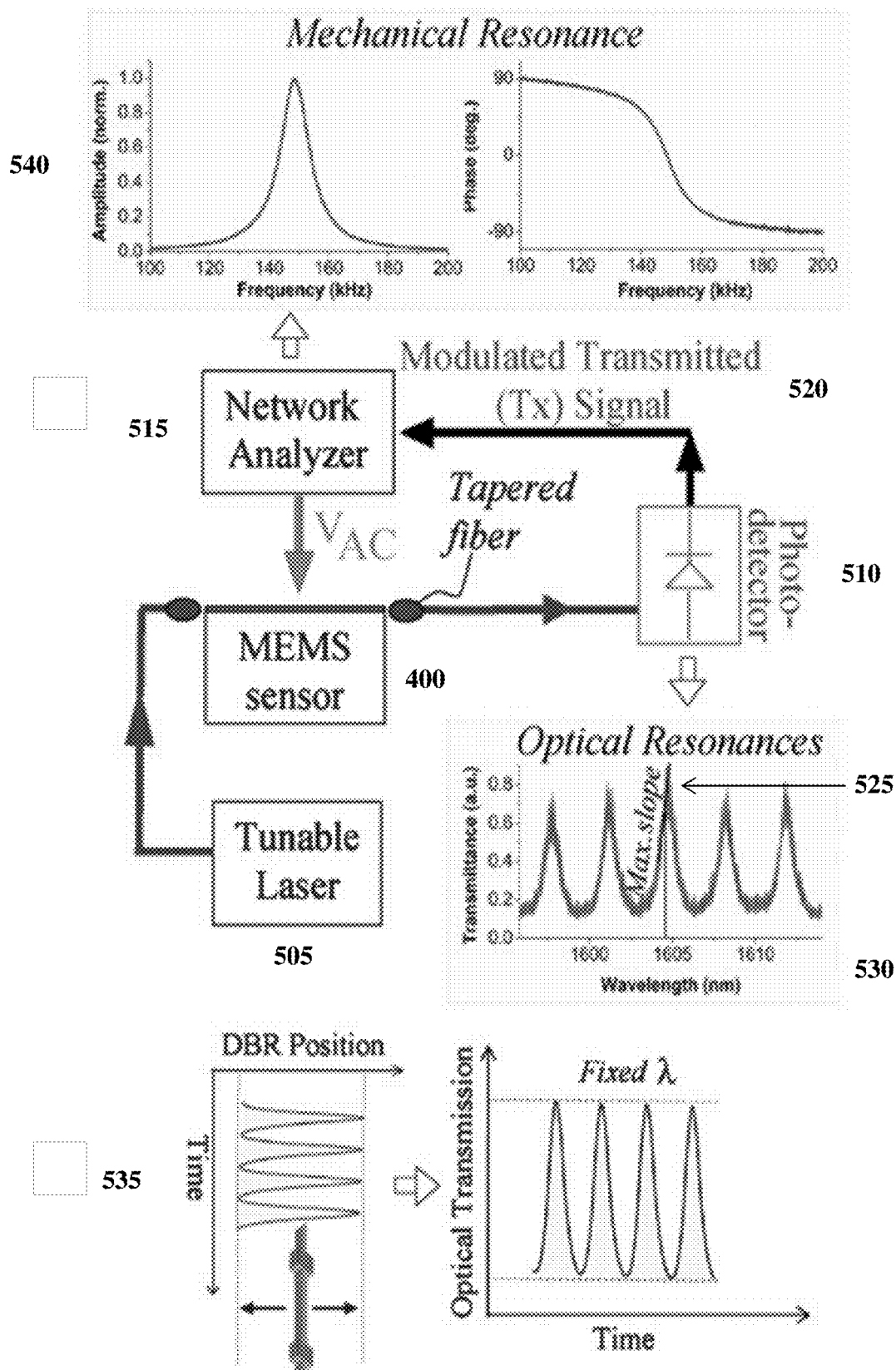
FIG. 5A is a schematic representing sensor measurements as performed with a mass sensor device, in accordance with an exemplary embodiment of the invention.

FIG. 5A is a schematic representing sensor measurements as performed with a mass sensor device, in accordance with an exemplary embodiment of the invention. Specifically, FIG. 5A represents the Fabry-Perot resonances of a mass sensor device 400 and a wavelength being set to the maximum slope 525. Sensing measurements can be performed using the setup in FIG. 5A. First, the Fabry-Perot optical resonances 530 can be measured by sweeping the laser wavelength and measuring the transmitted signal 520. Next, the wavelength can be fixed to the maximum slope 525. This can ensure efficient modulation of the microcavity transmittance as the MEMS microbridge and DBR mirror oscillate, as represented by the graphs 535. A network analyzer 515 can provide a frequency-swept voltage to the sensor 400 electrodes for electrostatic actuation in order to drive the MEMS microbridge 410 to resonance, as represented by the graphs 540. The microbridge motion can modulate the optical signal, which can then be detected and sent to the network analyzer 515. This can allow the MEMS microbridge amplitude and phase response to be measured, as represented by the graphs 540.

Figure 5B:
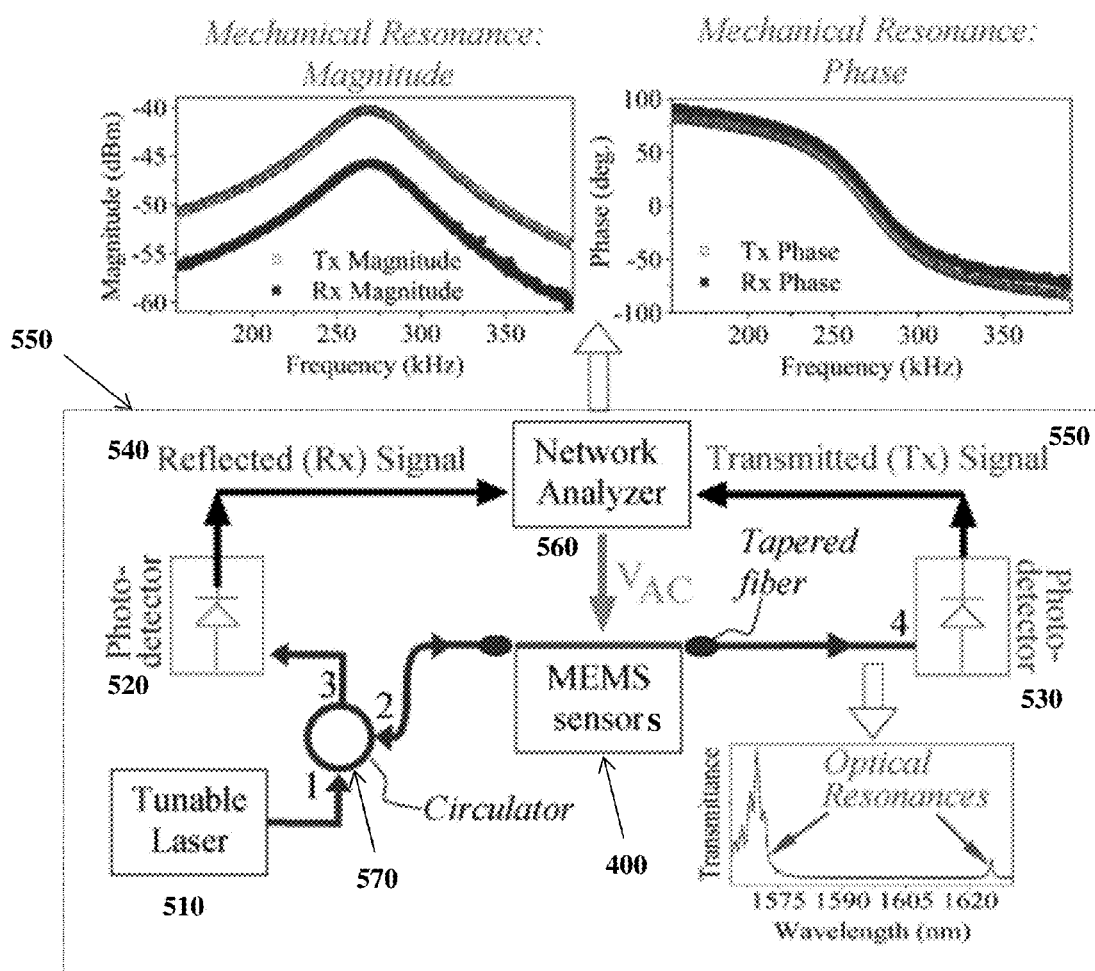
FIG. 5B is a schematic representing sensor measurements as performed with a mass sensor device where both transmitted and reflected signals can be measured, in accordance with an alternative exemplary embodiment of the invention.

In an exemplary embodiment of the invention, multiple exemplary mass sensor devices 400, as described above, can be incorporated in a mass sensor system 550, or mass sensor array. FIG. 5b is a schematic representing sensor measurements as performed with a mass sensor device in a mass sensor system where both transmitted and reflected signals can be measured, in accordance with an alternative exemplary embodiment of the invention. The ultimate goal of the exemplary mass sensor device 400 is to demonstrate compact size with high selectivity and high sensitivity to a broad range of chemical analytes. The development of large sensor arrays on a microfabricated chip can help obtain that goal. The mass sensor devices 400, owing to their in-plane configuration and interrogation via integrated optical waveguides, have few limitations in terms of numbers of sensors that can be incorporated on a single chip.

The mass sensor system 550 can include a plurality of mass sensors 400 connected in parallel via a plurality of waveguides. Though not illustrated, the MEMS sensors 400 box in FIG. 5B can include many, potentially hundreds or more, individual mass sensor devices 400. The plurality of mass sensors 400 can each include a microbridge 410 having a fundamental resonance frequency that includes a movable reflective mirror 448, which can be etched in a selected region of the microbridge 410. One or more chemoselective materials 460 can also be deposited on the microbridge 410. By coating each microbridge 410 with a different chemoselective material 460, or polymer, selectivity to various analytes can be demonstrated; and different analyte mixtures can be measured using the sensor array approach.

Each sensor can also include a fixed reflective mirror 444 that can be etched in a substrate, and the fixed reflective mirror 444 can be fixed to the substrate in a region spaced apart from the microbridge 410 and the movable reflective mirror 448. An optical, or rib, waveguide 430 can be etched in the substrate and can connect the movable mirror 448 and the fixed mirror 444 forming a Fabry-Perot microcavity interferometer 450. Finally, each of the mass sensors 400 can have an amplitude modulated voltage applied to one or more electrodes 420 surrounding the microbridge 410, thereby applying an electrostatic force and exciting the microbridge 410 at its fundamental resonance frequency. The amplitude modulated voltage can be applied by a voltage source.

In addition to the plurality of mass sensor devices 400, the exemplary mass sensor system 550 can include a tunable laser 555 operative to optically interrogate the Fabry-Perot microcavity interferometer 450 of each of the plurality of mass sensors 400. Furthermore, the mass sensor system 550 can include one or more receivers 560 and 565, or photodectors, operative to receive sensor signals 570 and 575 from each of the plurality of mass sensors 400, the sensor signals comprising reflective signals 570 and transmitted signals 575. In one embodiment the receiver 560 and 565 and the tunable laser 555 can be part of a common assembly separate from the mass sensor system 550. The incorporation of a fiber circulator 585 in the mass sensor system 550 setup can allow the measurement of both the transmitted signals 575 and reflected signals 570.

Figure 6:
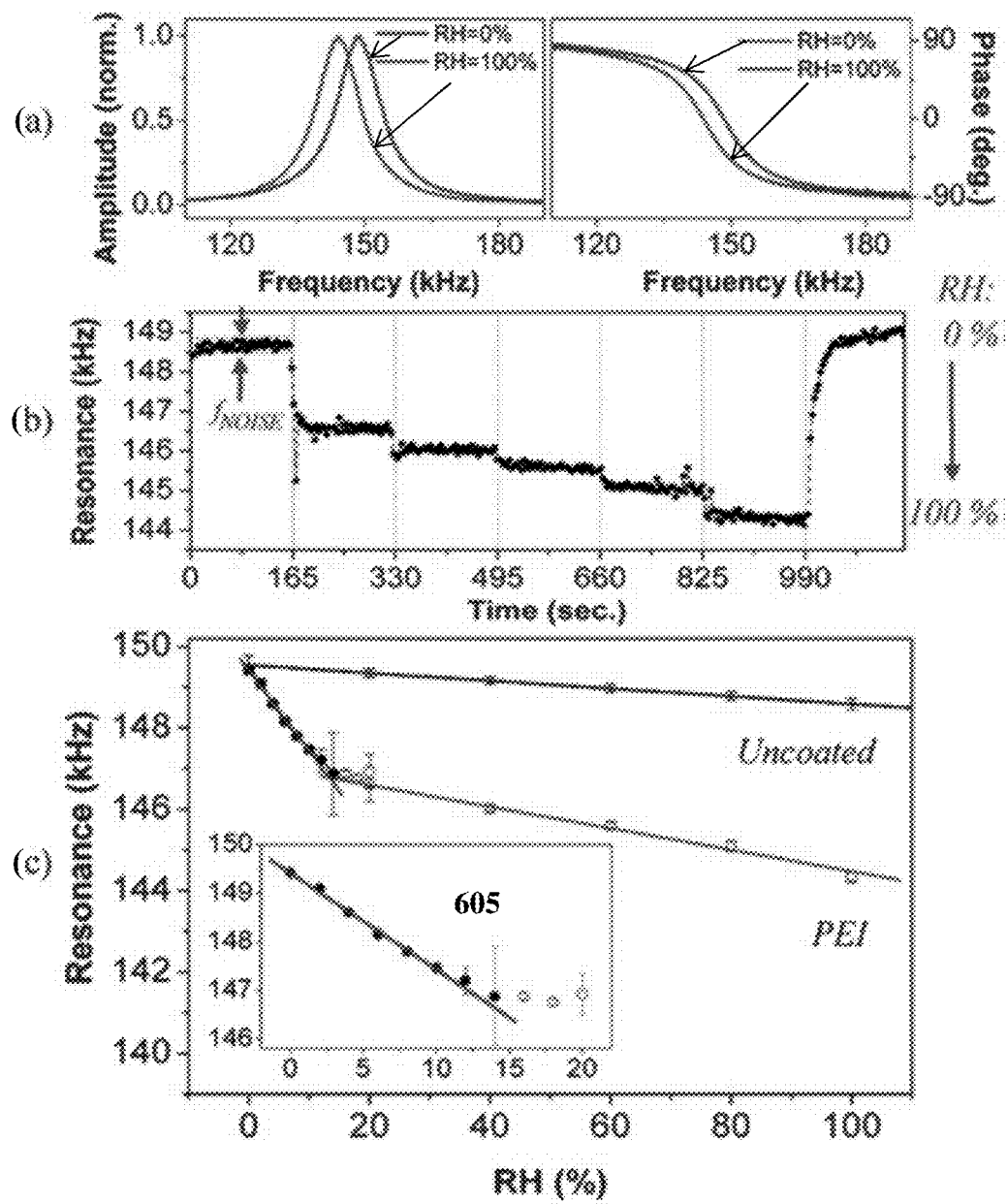
FIG. 6 represents experimental data from sensing and measuring relative humidity utilizing an exemplary sensor device in a sensor system, in accordance with an exemplary embodiment of the invention.

FIG. 6 represents experimental data from sensing and measuring relative humidity utilizing an exemplary sensor device 400 in a sensor system, in accordance with an exemplary embodiment of the invention. More specifically, the experimental results depict how the resonant frequency can decrease as a sensor device 400 is exposed to chemicals.

For the experimental results in FIG. 6, initial relative humidity sensing was performed by varying RH=0%-100%. The measured resonance amplitude and phase for RH=0% and 100% is represented in chart (a). Either the measured resonance amplitude or the phase can be used to extract the resonant peak ($f_0$). In this example, the amplitude measurement was utilized. Chart (b) represents the measured frequency response as the relative humidity is ramped up from RH=0%-100% in steps of 20%, and then scaled back to RH=0%. From this data, the network analyzer 560 can extract the resonant frequency. The resonant frequency is plotted as a function of RH in chart (c). For each RH value, fifty points of data can be measured, and these points can be used to extract an average as well as a measure of the frequency noise.

As represented in the charts of FIG. 6, the frequency shift for RH=0%-20% shows a strong response to water vapor. Therefore, more detailed humidity sensing can be performed by varying RH=0%-20% in steps of 2%, as represented by inset 605 in chart (c). For low humidity levels (e.g., RH<15%) the response can show a slope $slope_{PEI(RH=0\%-14\%)}$=−0.1975 kHz/RH. As a comparison, when an identical sensor 400 is tested before coating with PEI, it shows only a small response with $slope_{UNCOATED}$=−0.0095 kHz/RH. An enhancement of 20.8 in mass-loading and resonant frequency shift can be extracted by comparing the PEI coated sensor with the uncoated device. This strong enhancement can confirm the high concentrating ability and sorption of water vapor due to the large partition coefficient of the PEI-coating. Although the PEI itself results in mass-loading, the large partition coefficient can imply even larger mass-loading from water absorption. Consequently, at RH=0% the PEI coated sensor's resonant frequency is only slightly lower than the uncoated sensor, as represented in chart (c).

Therefore, the sensor device 400 can show large dynamic range with response to water vapor for RH=0%-100%. For the humidity range RH=20%-100%, a linear resonant frequency shift and response $slope_{PEI(RH=20\%-100\%)}$=−0.0265 kHz/RH, can be extracted. By comparing the slope for the PEI and uncoated measurements, an enhancement in mass loading of 2.8 for the PEI-coated sensor can be obtained. The response for large humidity (RH=20%-100%) can be significantly lower than for small humidity (RH<15%). This reduction in sensitivity can be explained by the absorption and saturation dynamics of the PEI coating, which can result in highest absorption sensitivity when the PEI is completely dehydrated, i.e. for low RH. The change in response slope for low vs. high RH is not seen in the uncoated device, confirming that the effect is entirely due to the PEI coating.

Figure 7:
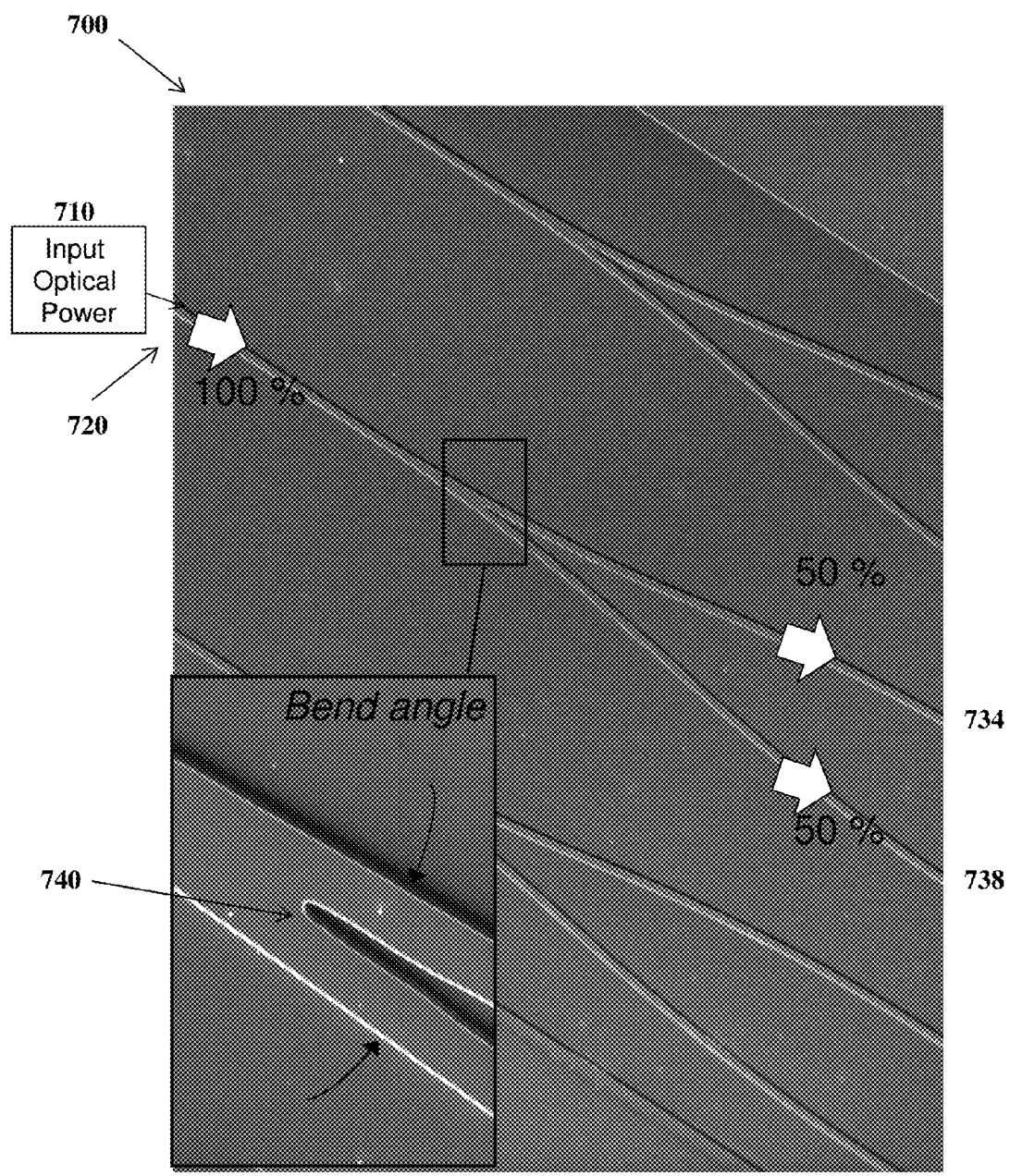
FIG. 7 represents a Y-branch waveguide for sending laser light from a single input to two or more sensors, in accordance with an exemplary embodiment of the invention.

In an exemplary embodiment, the mass sensor system 550 can include a plurality of waveguides in order to connect the plurality of mass sensor devices 400 in parallel. FIG. 7 represents a Y-branch waveguide 700 for sending laser light from a single input to two or more sensors, in accordance with an exemplary embodiment of the invention. In the exemplary embodiment, the plurality of waveguides take the form of a Y-branch waveguide 700, wherein an input optical power 710 that transmits a wavelength of laser light can be coupled at a single Y-input 720 and the plurality of sensors (not represented in FIG. 7, but see FIG. 8) are connected at a plurality of Y-outputs 715 and 738, wherein each sensor corresponds to an individual Y-output 715 and 738. For example, one sensor 400 can correspond to Y-output 715 and a second sensor 400 can correspond to the Y-output 738. In the Y-branch waveguide 700 the input optical power 710 is split evenly between the plurality of Y-outputs 715 and 738 of the Y-branch waveguide 700. As represented, the Y-branch waveguide merely illustrates a Y-branch waveguide with two outputs 715 and 738; however, one of ordinary skill in the art would understand that a Y-branch waveguide with many more outputs (e.g., potentially hundreds or more) can be utilized to connect the plurality of mass sensor devices 400. In an alternative exemplary embodiment, a directional coupler waveguide splitter could be utilized.

A Y-branch waveguide 700 is a power splitter that has application in large-scale sensor arrays such as the exemplary mass sensor system 550. A Y-branch waveguide can also be used as a power combiner. On-chip power splitters and combiners, such as the Y-branch waveguide 700, can enable multiple sensors to be interrogated using a single input/output waveguide. In a Y-branch waveguide 700 the bend angle 740 typically determines the total splitter length, because the waveguides need to be separated sufficiently to avoid crosstalk between the two outputs 715 and 738. For the exemplary waveguide, the input optical power 710 is represented as $P_{input}$=100%, and for identical output waveguides 715 and 738, the splitting ratio is $P_{715}$=$P_{738}$=50%. In an exemplary embodiment of the invention Y-branch waveguide splitters with bend angle 740 of α=0.5° can produce a minimum excess splitting loss of approximately 0.97 dB. Y-splitters with different bend angles, such as α=0.5-3.0°, can also be utilized. Additionally, by decreasing the bend angle (i.e., α<0.5°) a further reduction in loss can be anticipated; however, possibly at the expense of a longer device length.

Figure 8:
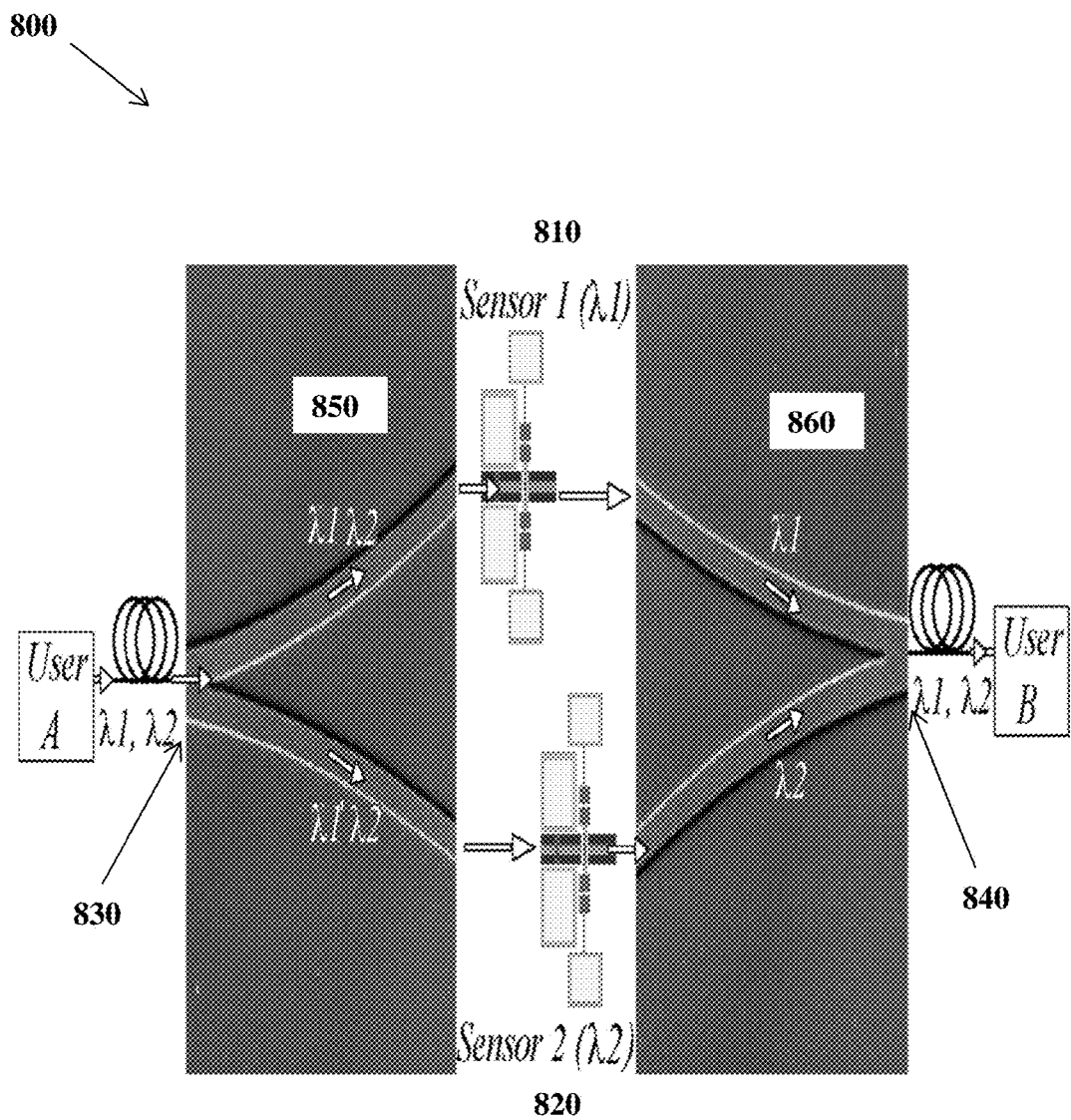
FIG. 8 is a further detailed drawing of two Y-branch waveguides in a mass sensor system, in accordance with an exemplary embodiment of the invention.

FIG. 8 is a further detailed drawing of two Y-branch waveguides 800 in a mass sensor system in accordance with an exemplary embodiment of the invention. Specifically, FIG. 8 represents a 1×2 sensor array architecture based on wavelength-division-multiplexing (WDM) techniques. As represented, the two Y-branch waveguides include two sensors 810 and 820, which can enable a single input/output for interrogating multiple sensors on-chip. The two sensors 810 and 820 can be embodiments of exemplary sensor device 400. Integrated waveguide power splitters can be used to measure each sensor 810 and 820. As shown in FIG. 8, second Y-branch waveguide 860 is connected to the output of the sensors connected to the first Y-branch waveguide 850 such that there can exist a single input waveguide 830 and a single output waveguide 840.

The Fabry-Perot microcavity of each sensor 810 and 820 can be designed so that Sensor 1 810 has an optical resonance wavelength λ1 and Sensor 2 820 has optical resonance λ2. For example, this can be accomplished by spacing apart the fixed reflective mirror 444 and the movable reflective mirror 448 that form the Fabry-Perot microcavity interferometer 450 for each of the sensors 810 and 820 at a different distance from each other, so that Fabry-Perot microcavity interferometer 450 of each of the sensors 810 and 820 can have a different optical resonant wavelength. In this manner, an end user may interrogate each sensor 810 and 820 by adjusting the wavelength of laser light sent to the sensors 810 and 820. More specifically, the optical resonant wavelength of each Fabry-Perot microcavity interferometer 450 of each of the sensors 810 and 820 (or the plurality of additional sensors 400 that can be attached in parallel) can be matched by varying the wavelength of laser light transmitted into the single Y-input 830.

After transmitting the input wavelength of laser light to the sensors 810 and 820, the sensor signals from each sensor 810 and 820 can then combined into a single output 840 to be received and measured by an end user. More specifically, the transmitted signals from each of the sensors 810 and 820 can be transmitted and measured at the single Y-output 840 of the Y-branch waveguide. In an alternative embodiment, reflective signals from each of the sensors 810 and 820 are reflected back to and measured at the single Y-input 830 of the Y-branch waveguide (see also FIG. 5B). In both cases, wavelength-division-multiplexing techniques can be used to separate the sensor signals from each of the mass sensors 810 and 820. By coating each sensor 810 and 820 in the array with a unique chemoselective polymer, the selectivity as well as the number of chemical analytes that can be sensed can be increased.

In an exemplary method of the invention, a method for sensing a change in mass of a microbridge in a mass sensor can be provided. A time-varying amplitude modulated electrostatic force can be applied to the microbridge 410, and the microbridge 410 can be excited into resonance at the frequency of amplitude modulation. Upon being excited into resonance, the microbridge 410 can move in a direction parallel to the substrate. More specifically, the amplitude modulated voltage can be applied to one or more electrodes 420 surrounding the microbridge 410, thereby generating the electrostatic force. However, the frequency of amplitude modulation of the applied voltage is offset from the fundamental resonance frequency of the microbridge 410.

In an embodiment of the invention, the frequency of the applied amplitude modulation voltage can be varied through a frequency range. The frequency range can include the resonance frequency of the microbridge 410 without sorbed chemical in a chemoselective layer 460 on the microbridge 410, and the resonance frequency of the microbridge 410 with sorbed chemical in a chemoselective layer 460 on the microbridge 410. In one embodiment, the sweeping of the frequency of amplitude modulation over a range of frequencies can be performed with a network analyzer 580, and the amplitude modulation can electrostatically excite the microbridge 410 at its fundamental resonance frequency.

Next, optical energy can be received from an input source at a wavelength that is close to a resonant wavelength of a Fabry-Perot microcavity interferometer. This wavelength can be represented by the maximum slope 525 as depicted in FIG. 5a. The optical energy can be provided by a tunable laser 555 that can generate the optical energy at a plurality of wavelengths. More specifically, the wavelength can be tuned to a side of a Fabry-Perot mode of a microcavity 525. The side of a Fabry-Perot mode of a microcavity refers to a wavelength that is very close, but slightly offset, to the minimum reflectance of the Fabry-Perot microcavity.

The movable reflective mirror 448 and fixed reflective mirror 444 can reflect the optical energy to one or more receivers, or photodectors 520 and 530. Finally, a change in reflectivity of the microbridge 410 can be interferometrically determined. The change in reflectivity can indicate a decrease in resonant frequency of the microbridge 410 due to the increased mass of the microbridge 410 resulting from sorption of a target chemical by a layer of chemoselective material 460 disposed on the microbridge 410. The change in resonant frequency of the microbridge due to increased mass of the microbridge can also indicate an amount of the target chemical sorbed by the chemoselective material. As discussed above, FIG. 6 represents the experimental data and represents how the resonant frequency can decrease with adsorption of the target chemical.

The MEMS sensor, in accordance with an exemplary embodiment of the invention, can be operated in two different modes. For example, in an exemplary first mode of the present invention, a microbridge displacement can cause the optical resonances to be shifted. This is a static mode and is known as strain loading. The optical transmittance, T, of a Fabry-Perot microcavity interferometer depends on the cavity length, $L_C$, as:

$$T(Lc) = \frac{T_0}{1 + (2F/\pi)^2 \sin^2(2\pi n_c L_c/\lambda)}, \qquad \text{(equation 1)}$$

where $T_0$ is the peak transmittance, λ is the laser wavelength, $n_C$ is the cavity refractive index, and $F=(\pi R^{1/2})/(1-R)$ is the finesse that describes the quality of the optical modes, where R is the DBR mirror reflectance. By displacing one of the DBR mirrors the Fabry-Perot modes, $\lambda_j$, are shifted:

$$\lambda_j(\Delta x) \approx 2\Delta x/(j+1), \qquad \text{(equation 2)}$$

where j is optical mode number. In one embodiment, mass sensors with finesse, F=265, DBR reflectance R=0.988, and Δλ>10 nm tuning have been demonstrated. If the MEMS microbridge is coated with a chemoselective polymer, then an induced strain gradient between the silicon bridge and chemoselective polymer can result in a bridge bending. For example, analyte exposure can result in mass adsorption, an induced strain (ε) in the polymer, strain-induced microbridge bending, Δx(ε), and a tuning of the Fabry-Perot resonance.

In another exemplary mode of the present invention, by fixing a laser wavelength, the microbridge displacement modulates the cavity transmittance. This is a dynamic mode, and known as mass loading.

If the laser wavelength is fixed, then any microbridge oscillation can modulate the DBR position and vary the cavity length, $L_C$, modulating the transmittance, T. The higher the DBR reflectance, R, the larger the optical modulation is versus the displacement. By measuring the modulated optical signal, the mechanical microbridge resonance can be measured. The MEMS microbridge can be excited by grounding the microbridge and applying an AC bias to the electrodes. The resonant frequency, $f_M$, for mode M of the bridge is:

$$f_M = \frac{1}{2\pi}\sqrt{\frac{k_{Effective}}{m_{Effective}}}, \quad \text{(equation 3)}$$

where $k_{Effective}$ and $m_{Effective}$ are the bridge effective mass and spring constant, respectively.

Exposure to an analyte can result in adsorption of the analyte by the chemoselective polymer, and mass-loading. The shifted resonant frequency can be obtained by replacing the $m_{Effective}$ in equation (3) with $m_{Effective} = m_{Effective(No\ Mass\ Loading)} + \Delta m_{Effective}$, where:

$$\Delta m_{effective} = \int_0^\infty \int_{-w/2}^{w/2} \int_{-L/2}^{L/2} s(x, y, z)\Phi_M^2(x, y, z)\,dx\,dy\,dz \quad \text{(equation 4)}$$

Here, s(x, y, z) describes the distribution of the adsorbed mass as a function of bridge position and $\phi_M(x, y, z)=\phi_M(z)$ is the mode shape function for the $M^{th}$ in-plane mechanical resonance. From equation 4, the location of the adsorbed mass and the mode number M determine the frequency shift; e.g., the fundamental mode (M=0) has largest response for mass loading at the bridge center, although higher-order modes (M>0) will behave differently. In particular, the use of higher-order modes may be exploited for enhanced sensitivity.

Assuming uniform analyte adsorption over the MEMS microbridge and no strain-induced change in the microbridge spring constant, the approximate normalized frequency shift is:

$$\frac{\Delta f_m}{f_0} = \sqrt{\frac{m_{effective}}{m_{effective} + \Delta m_{effective}}} - 1 \approx \frac{1}{2}\left(\frac{\Delta m_{effective}}{m_{effective}}\right), \quad \text{(equation 5)}$$

where $m_{effective}=0.73\ \rho Ltw$ for the fundamental resonance mode and ρ is silicon's mass density.

In an exemplary embodiment of the invention, polyethyleneimine (PEI) can be used to coat the sensor. PEI is a commercial polymer that has a strong affinity for water vapor. The ability to adsorb and concentrate a chemical analyte is given by the partition coefficient, $K=C_S/C_V$, where $C_S$ is the concentration of analyte in the sorbent phase (i.e. adsorbed by the chemoselective polymer), and CV is the concentration in the vapor phase (i.e. in the environment). The partition coefficient of PEI for water vapor is $K_{PEI,\ H2O}\approx 100,000$. Therefore, this chemoselective polymer can be a suitable candidate for proof-of-principle humidity sensing, as a large degree of sorption and concentration can be expected. Other chemoselective polymers can be substituted for other sensing applications (e.g. explosives, toxic gas, etc.)

Returning to FIG. 5B, it can be used to depict the two different mass sensor system sensing modes discussed above. For strain loading, a tunable laser 555 can couple laser light to the sensor 400 via tapered optical fibers. On the input side, a fiber circulator 585 can separate the reflected signal from the incident laser probe signal. Photodetectors 560 and 565, or receivers, on both the transmitted side 570 and reflected sides 575 can measure the optical signal. Measurements on both sides can be equivalent. For adsorption-induced strain and bending, static mode/strain loading, the Fabry-Perot microcavity 450 is passive, and the optical resonances can be continuously measured as the sensor is exposed to various analytes. Exposure to analytes can induce strain in the polymer, which can bend the microbeam and tune the Fabry-Perot microcavity resonances.

For mass-loading based mechanical resonance measurements, the optical signal can be sent to a network analyzer 580, which can also supply a frequency-swept actuation voltage to drive the MEMS microbridge resonances. The microbridge oscillation modulates the Fabry-Perot microcavity transmittance. This can enable the measurement of both the magnitude and phase. With the laser probe fixed at the peak-slope wavelength of a Fabry-Perot optical resonance, the MEMS microbridge resonance can excited by sweeping the AC actuation voltage from the network analyzer 580. The sensor 400 can then be exposed to chemical vapors and the shift in mechanical resonance frequency is measured over time. As discussed above, FIG. 6 experimental data and shows how the resonant frequency can decrease with adsorption of the target chemical.

As noted previously, both transmitted ($T_X$) signals 550 and reflected ($R_X$) signals 540 from an exemplary mass sensor 400 can be used for sensing. The Fabry-Perot transmittance is given by equation (1) above, while the reflectance is simply the complement, $R(L_C)=1-T(L_C)$. Consequently, any modulation of $T(L_C)$ can also modulate the reflected signal. FIG. 5B represents an agreement between $T_X$ and $R_X$ signals. Therefore, either signal can be used for interrogating the sensor 400. For example, the $T_X$ signal 550 can be useful for sending the sensor data to an external operator, who may receive the signal via a fiber optic network. In this configuration, the sensor requires a laser source, either on-chip or coupled at the input. In contrast, the $R_X$ signal 540 can be useful for an operator with a laser source who wishes to send a laser pulse down an optical network with the sensor reflecting the data back to the operator. Therefore, in this alternative example, the sensor is passive and does not require a laser on-chip.

As noted, the features of the exemplary mass sensor device and system disclosed herein have a number of advantages over existing MEMS sensor designs. For example, the optical methods enable high-sensitivity displacement measurements. In particular, the use of interferometry enables displacement measurements with resolution much smaller than the wavelength of light used. By integrating a Fabry-Perot interferometer with a waveguide, as described in the exemplary invention herein, it is possible to minimize optical losses, increase the optical Q, and thereby enhance the sensitivity of the interferometer. In fact, the exemplary invention described herein enables high resolution measurements of Brownian noise within the MEMS sensor with resolution better than 10 fm/Hz$^{1/2}$. Such Brownian noise results from random temperature fluctuations in the environment that can couple to the MEMS resonator and induce mechanical resonances. The higher the sensitivity, the smaller the displacements that can be measured and the smaller the actuation voltage (power) that is required to operate the sensor.

A second advantage of the exemplary invention described herein is the possibility of high optical quality factor (Q) and high finesse (F) waveguide Fabry-Perot microcavities. Devices with Q=27,000 and F~500 can be accomplished. Such high performance can enable the interrogation of multiple sensors on a single chip by addressing each sensor with a different optical wavelength. If each sensor is designed with a Fabry-Perot microcavity with unique optical resonance wavelength, then each sensor will also only respond to a unique wavelength. As mentioned, it is possible to design a single input/output waveguide, which can be used to interrogate multiple sensors using waveguide splitters and combiners. This approach by itself will not discriminate between individual sensors. However, the wavelength-selective interrogation afforded by the Fabry-Perot microcavities is a key component to enabling large-scale single-chip sensor arrays.

Another advantage of the exemplary invention described herein, is that the electrostatic actuation mechanism that is used to excite mechanical resonances allows higher-order resonances to be excited. For example, if the MEMS microbridge in FIG. 4 is grounded and an AC voltage is applied to both metal electrodes, then the fundamental in-plane mechanical resonance is excited. However, if the AC bias is applied to only one of the two electrodes, then the second order in-plane resonance is excited. Higher-order modes typically exhibit higher mechanical Q-factors and enable enhanced sensitivity. However, higher-order modes typically also exhibit reduced displacement amplitude, which makes their measurement difficult. The present invention has the advantage of utilizing a high-Q optical microcavity that enables extremely small displacements to be measured, in the picometer range. Furthermore, the placement of several actuation electrodes along the length of the MEMS microbridge enables the preferential excitation of arbitrary higher-order modes for enhanced sensitivity.

Besides the potential for enhanced sensitivity, the operation at higher order modes can serve as an on-chip reference signal. Mass loading is described by the effective mass change in equation (4) above and depends on two factors: (1) the location of the adsorbed mass (analyte), s(x, y, z) on the MEMS microbridge, and (2) the excited mechanical resonance mode, $\phi_M(x, y, z)$. Therefore, by placing the chemoselective polymer on only selected areas on the microbridge, it is possible to operate the sensor so that mode $M_1$ will exhibit mass loading ($\Delta m_{Effective} > 0$) while mode $M_2$ does not exhibit a change in effective mass ($\Delta m_{Effective} = 0$). Operation at mode $M_2$ can then serve as a reference mode, one that is not affected by chemical analytes, adsorption, and mass loading. Previously, an array of MEMS bridges was used in which one bridge was left uncoated (no chemo-selective polymer) to serve as a reference bridge for compensating changes in temperature, for example. In the exemplary invention described herein, changing the mechanical resonance mode can enable a single device to serve as both the sensing as well as the reference bridge.

Figure 9:
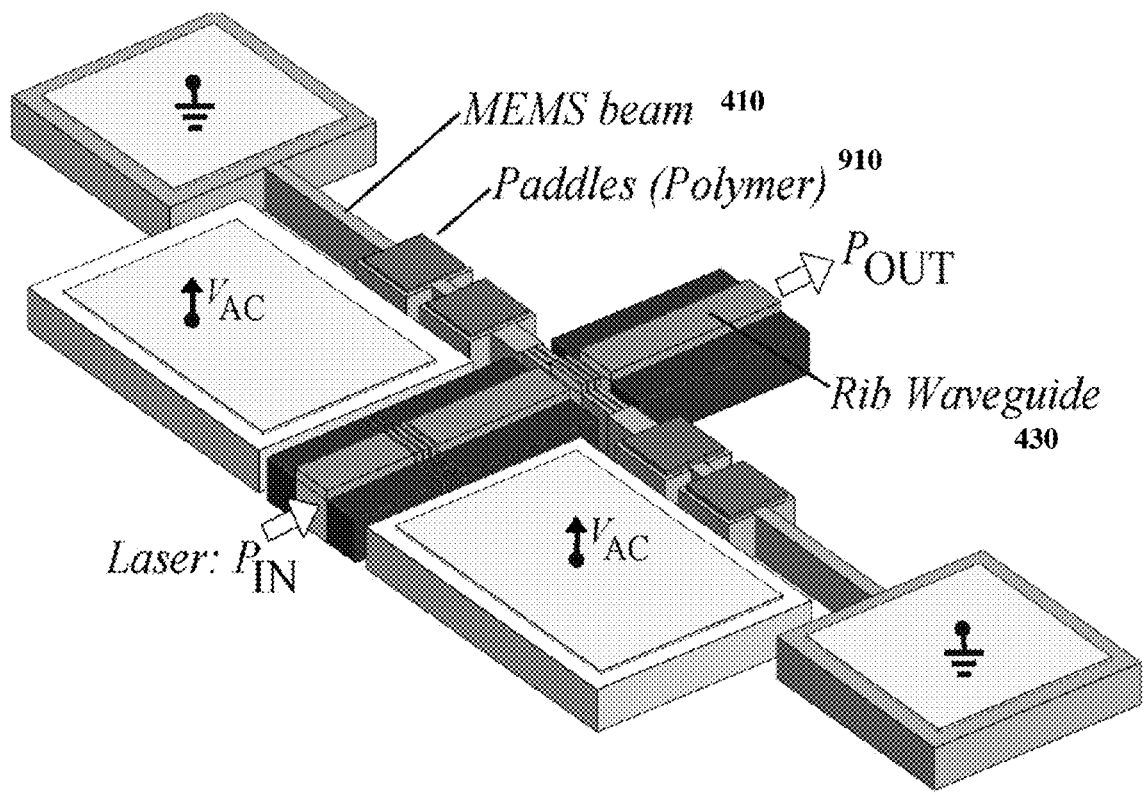
FIG. 9 is a further detailed schematic of a MEMS sensor showing dedicated paddles for ease of chemoselective polymer deposition, in accordance with an exemplary embodiment of the invention.

FIG. 9 is a further detailed schematic of a MEMS sensor showing dedicated paddles for ease of chemoselective polymer deposition, in accordance with an exemplary embodiment of the invention. A microbridge 410 is represented with four square-shaped (e.g., 8 mm×8 mm) paddles 910. Other numbers, or sizes, of paddles can also be utilized. In an alternative exemplary embodiment, the paddles 910 can each provide a specific location on the microbridge 410 in which to deposit a chemoselective polymer. Thus, these paddles 910 can simplify the deposition of chemoselective polymers, whose purpose is to selectively absorb a chemical analyte of interest resulting in mass loading and a decrease in the MEMS bridge resonant frequency. In another alternative embodiment, different chemoselective materials can be deposited on each of the paddles 810 on a microbridge 410.

Furthermore, the paddles 910 can be designed to be rigid compared to the MEMS microbridge (e.g., $W_{Bridge}$=1.5 µm, $L_{Bridge}$=300 µm). This rigidity can ensure that the bridge spring constant is not affected by any strain induced by coating the paddles 910 with a polymer. Typically during sensing the chemoselective polymer can swell significantly due to absorption of chemical analytes, potentially straining the MEMS microbridge and complicating the sensor readout. However, although strain-induced bending may be useful for biological sensors operating in aqueous environments, this mode of operation is generally not desired for mass-loading based devices. The rigid paddles of the alternative exemplary embodiment can minimize strain induced by the polymer swelling during exposure to chemicals, thereby minimizing beam bending due to strain.

Figure 10:
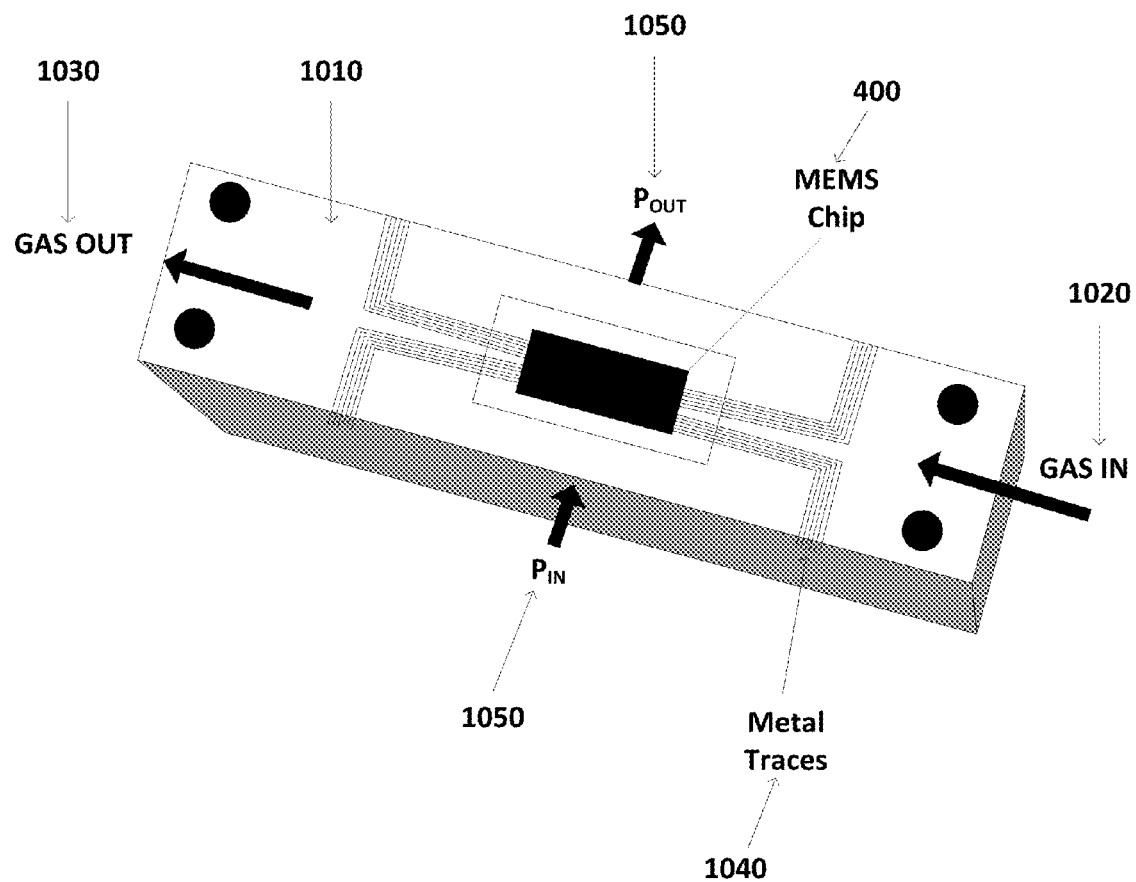
FIG. 10 is a picture depicting how a sensor device can be packaged, in accordance with an exemplary embodiment of the invention.

FIG. 10 is a picture depicting how a sensor device can be packaged, in accordance with an exemplary embodiment of the invention. The exemplary packaging can allow the sensor device 400 to be packaged in a flow cell 1010 with electrical connections and optical fiber connections for accessing and interrogating each sensor 400 individually. More specifically, the sensors 400 can be packaged in a custom plexiglas flow cell 1010 to ensure controlled and repeatable sensing without interference from the outside (lab) environment. Inlet ports 1020 and outlet ports 1030 can be used to introduce dry N2 gas with trace amounts of chemical analyte to be sensed. The small flow cell volume (0.24 cm3) can ensure fast equilibrium time enabling accurate sensor measurements. The sample can be mounted on a circuit board and gold wires can be bonded to the sample and metal traces 1040 on the board. In one embodiment, an optical epoxy (e.g., Epoxy Technology, Epotek 310) can be applied to the bottom surface of the flow cell 1010 and cured at 60° C. The epoxy can form an "O-ring" seal once the flow cell 1010 is attached to the circuit board and chip. The packaging can enable electrical contact with metal traces 1040 on the circuit board; optical coupling to the waveguide facets can be performed with lensed fibers. The waveguide facets 1050 can be located outside of the flow cell 1010, but part of the waveguide can be covered with epoxy in order to seal the MEMS sensor 400 inside the flow cell 1010. The optical loss due to the epoxy is minimal (e.g., <0.5 dB). Other alternative means of sensor packaging can also be utilized.

Other alternative embodiments of the invention can also be provided. As described above, the sensors 400 are electrostatically actuated via an AC drive voltage to excite the mechanical resonances. In an alternative embodiment, it can be possible to use photothermal actuation to excite the bridge resonances. In this exemplary alternative embodiment, a single continuous wave (CW) laser can be used for sensing a change in the mass of the microbridge in the sensor and for exciting the microbridge resonance such that no voltage needs to be applied to the sensor. The use of the single CW laser can result in photothermal heating. The photothermal heating can causes the microbridge to expand at the movable reflective mirror region, typically the center of the microbridge. The expansion at the center of the microbridge can result in the buckling of the microbridge and the movable reflective mirror moving in on the microbridge. The moving of the movable reflective mirror can tune the Fabry-Perot microcavity. The tuning of the Fabry-Perot microcavity can reduce the amount of photothermal heating; thereby, cooling the movable reflective mirror and the microbridge. Eventually, the cooling can cause the microbridge to decrease buckling and return to its original position.

Figure 11:
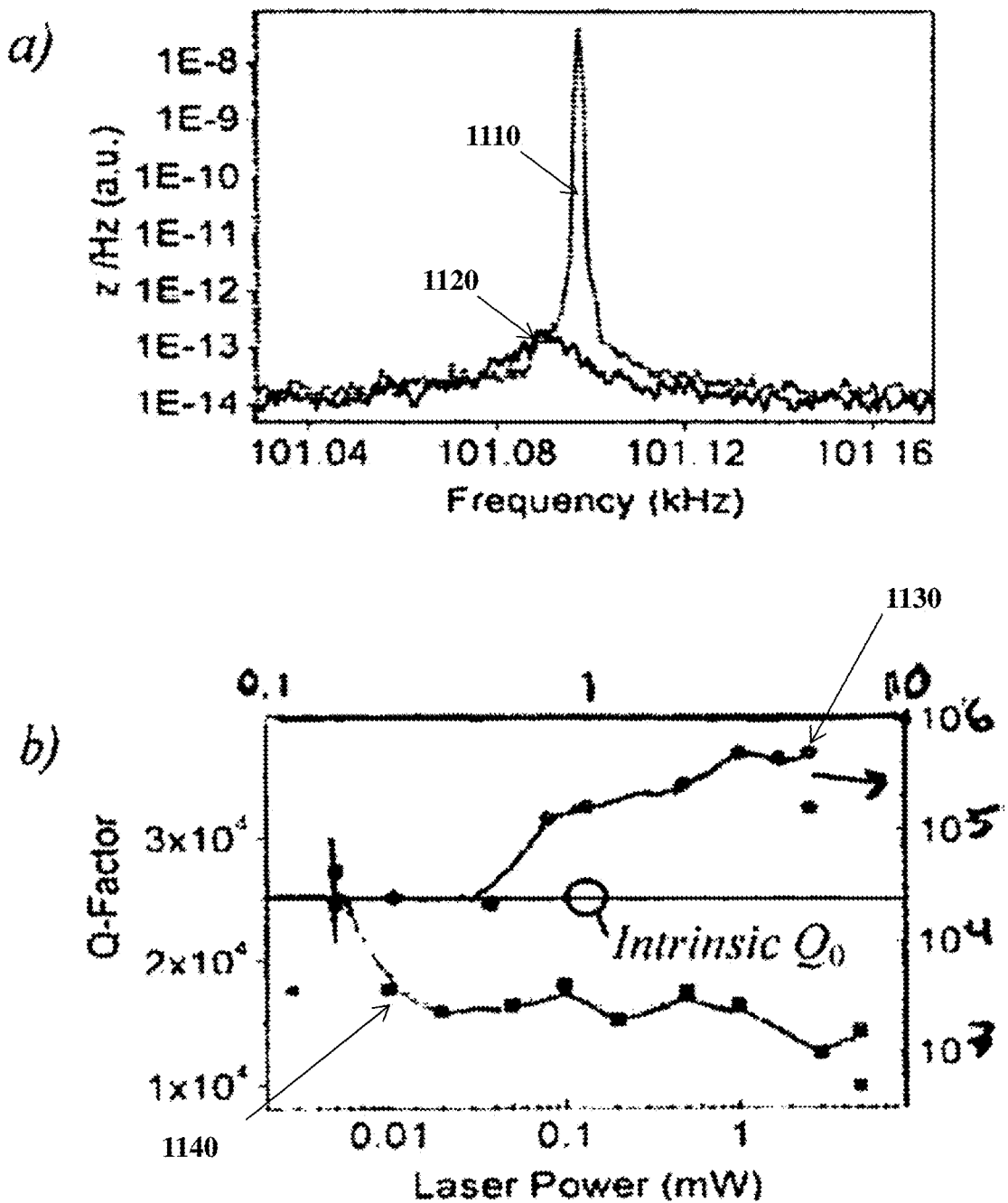
FIG. 11 represents experimental data demonstrating how the mechanical Q-factor depends on the wavelength and power of the laser, in accordance with an exemplary embodiment of the invention.

In this exemplary alternative embodiment, the CW laser can cause repeated photothermal heating and cooling. The repeated photothermal heating and cooling can be used to excite the mechanical resonance of the microbridge, avoiding the need for electrical power. By varying the laser wavelength and power, it can be possible to drive the microbridge to resonance as well as change the mechanical Q-factor (amplification and damping of motion), as shown in FIG. 11. For example, the experimental data in FIG. 11A represents how the microbridge vibration amplitude can be increased sharply, represented by line plot 1110 on the chart, by setting the laser wavelength to wavelength $\lambda_1$. In contrast, if the laser wavelength is changed to $\lambda_2$ the microbridge vibration amplitude is strongly dampened, represented by line plot 1120 on the chart. FIG. 11B represents additional experimental data depicting the effect on the value of a mechanical Q-factor depending on the wavelength and power of the laser, in accordance with an exemplary embodiment of the invention. As depicted in FIG. 11B, the mechanical Q-factor of the microbridge can be increased, represented by line 1130 on the chart, or decreased, represented by line 1140 on the chart, by increasing the laser power, as well as by varying the laser wavelength.

In an alternative exemplary embodiment, the sensors can utilize radiation pressure in place of photothermal effects to drive the mechanical resonances. This second exemplary method also avoids the need for electrical power. Additionally, by utilizing radiation pressure, the mechanical Q-factor of the microbridge can be increased or decreased by increasing the laser power, as well as by varying the laser wavelength.

In another alternative embodiment, photodetectors can be incorporated on the chip. The photodetectors can then detect laser light and convert it into an AC drive voltage for actuating the bridges. Once again, this avoids the need for electrical power.

In another alternative embodiment, the microbridge cannot have a voltage applied to it. In this alternative embodiment, when sorption of a target chemical by a chemoselective material on the microbridge induces swelling of the chemoselective material, the swelling can cause the microbridge to bend in a manner that corresponds to the concentration of the chemical.

As described above, the sensors 400 are made of silicon—generally an optically inactive material. However, in an alternative embodiment, a different semiconductor could be used for the production of the sensors 400. For example, it can be possible to fabricate the semiconductor devices from active materials, such as, e.g. indium phosphide or gallium arsenide. Active material semiconductors can enable the integration of laser sources on chip.

Typically Fabry-Perot microcavities 450 can be considered 1-dimensional (1-D) photonic crystals. However, photonic crystals also consist of microcavities that offer 2-D or 3-D light confinement and can be made much more compact than the Fabry-Perot microcavities 450 described herein. In an alternative exemplary embodiment, the sensors 400 can be further miniaturized by replacing the 1-D Fabry-Perot microcavity 450 with a 2-D (or 3-D) photonic crystal microcavity.

Finally, the sensor can be modified to function as an accelerometer. In this alternative embodiment, the MEMS microbridge can include a proof mass. The microbridge, and proof mass, resonance can be modified in the presence of accelerating forces. The shift in resonance can be measured using the on-chip interferometer.

It should be understood that the foregoing relates only to illustrative embodiments of the present invention, and that numerous changes may be made therein without departing from the scope and spirit of the invention as defined by the following claims.

The invention claimed is:

1. A mass sensor system comprising:
a plurality of mass sensors, arrayed on a single chip, comprising respective Fabry-Perot microcavities connected in parallel via a plurality of waveguides;
a laser operative to optically interrogate the Fabry-Perot microcavity of each of the plurality of mass sensors; and
a receiver operative to receive sensor signals from each of the plurality of mass sensors, the sensor signals comprising reflective signals and transmitted signals.

2. The mass sensor system of claim 1, wherein the plurality of mass sensors each comprise:
a microbridge having a fundamental resonance frequency and comprising a movable reflective mirror etched in a selected region of the microbridge, wherein a change in mass results in a change in the fundamental resonance frequency of the microbridge oscillator;
a fixed reflective mirror etched in a substrate, the fixed reflective mirror being fixed to the substrate in a region spaced apart from the microbridge and the movable reflective mirror; and
an optical waveguide etched in the substrate between the movable mirror and the fixed mirror forming the Fabry-Perot microcavity interferometer;
wherein the laser comprises a continuous-wave laser source, wherein the continuous-wave laser source enables optical readout of the motion of the microbridge; and wherein the continuous-wave laser source generates optical forces that excite the microbridge at its fundamental resonance frequency and the optical forces modify the motion, dynamics, or mechanical Q-factor of the microbridge.

3. The mass sensor system of claim 2, wherein the microbridge comprises a proof mass.

4. The mass sensor system of claim 3, wherein a change in resonant frequency of the microbridge and the proof mass is used to indicate and measure acceleration.

5. The mass sensor system of claim 4, wherein a plurality of individual mass sensors in the mass sensor system each measure acceleration in a different direction providing a measurement of acceleration in all directions.

6. The mass sensor system of claim 1, further comprising:
a common assembly separate from the mass sensor, the common assembly comprising:
the receiver; and
the tunable laser.

7. The mass sensor system of claim 1, wherein the plurality of waveguides take the form of a first Y-branch waveguide, wherein an input optical power that transmits a wavelength of laser light is coupled at a single Y-input and the plurality of sensors are connected at a plurality of Y-outputs, wherein each sensor corresponds to an individual Y-output.

8. The mass sensor system of claim 7, wherein the input optical power is split evenly between the plurality of Y-outputs of the first Y-branch waveguide.

9. The mass sensor system of claim 7, wherein the reflective signals from each of the plurality of mass sensors are reflected back to and measured at the single Y-input of the first Y-branch waveguide.

10. The mass sensor system of claim 7, wherein the transmitted signals from each of the plurality of mass sensors are transmitted and measured at the corresponding Y-output of the sensor.

11. The mass sensor system of claim 7, wherein a second Y-branch waveguide is connected to the output of the plurality of sensors connected to the first Y-branch waveguide creating a single input waveguide and a single output waveguide.

12. The mass sensor system of claim 11 wherein the sensor signals are measured at the single output waveguide.

13. The mass sensor system of claim 1, wherein each Fabry-Perot microcavity has a different optical resonant wavelength.

14. The mass sensor system of claim 13, wherein the optical resonant wavelength of each Fabry-Perot microcavity of the plurality of sensors is matched by varying the wavelength of laser light transmitted into a single Y-input.

15. The mass sensor system of claim 1, wherein dense-wavelength-division-multiplexing techniques are used to separate sensor signals from each of the plurality of mass sensors.

16. The mass sensor system of claim 1, wherein the mass sensor system is packaged in a flow cell with optical fiber connections for coupling laser light to and from each of the plurality of mass sensors individually.

17. The mass sensor system of claim 1, wherein the mass sensor system is configured to function as a 3-axis accelerometer.

18. The mass sensor system of claim 1, wherein the plurality of mass sensors, the tunable laser, and the optical receiver are fabricated on a single fully-integrated circuit on a common substrate of the single chip.

19. The mass sensor system of claim 1, wherein the respective Fabry-Perot microcavities are high-finesse Fabry-Perot microcavities.

20. The mass sensor system of claim 1, wherein the sensors and the waveguides are fabricated on a common substrate.

* * * * *